US006951736B2

(12) United States Patent
Ivarie et al.

(10) Patent No.: US 6,951,736 B2
(45) Date of Patent: Oct. 4, 2005

(54) AVIAN *MAGO NASHI* GENE

(75) Inventors: Robert D. Ivarie, Watkinsville, GA (US); Tracy M. Andacht, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 685 days.

(21) Appl. No.: 09/788,773

(22) Filed: Feb. 20, 2001

(65) Prior Publication Data

US 2003/0092146 A1 May 15, 2003

(51) Int. Cl.[7] .......................... C12P 21/06; C07H 17/00; C07K 14/00
(52) U.S. Cl. ................ 435/69.1; 435/320.1; 435/252.3; 435/325; 536/23.1; 530/350
(58) Field of Search ........................ 536/23.1; 530/350; 435/69.1, 320.1, 252.3, 325

(56) References Cited

U.S. PATENT DOCUMENTS 5,807,708 A * 9/1998 Falb et al. ................. 435/69.1

OTHER PUBLICATIONS

"Mutations in a newly identified Drosophila melanogaster gene, *mago nashi*, disrupt germ cell formation and result in the formation of mirror–image symmetrical double abdomen embryos"; R.E. Boswell, M.E. Prout, J.C. Steichen, Development 113, 373–384, 1991.

"The *mago nashi* locus encodes an essential product required for germ plasm assembly in Drosophila"; P.A. Newmark, R.E. Boswell, Development 120, 1303–1313, 1994.

"Posterior localization of the Drosophilia Giα protein during early embryogenesis requires a subset of the posterior group genes"; W.J. Wolfgang, M. Forte, Int. J. Dev. Biol. 39, 581–586, 1995.

"*Mago nashi* mediates the posterior follicle cell–to–oocyte signal to organize axis formation in Drosophila"; P.A. Newmark, S.E. Mohr, L. Gong, R.E. Boswell, Development 124, 3197–3207, 1997.

"The *mago nashi* gene is required for the polarisation of the oocyte and the formation of perpendicular axes in Drosophila"; D.R. Micklem, R. Dasgupta, H. Elliott, F. Gergely, C. Davidson, A. Brand, A. Gonzalez–Reyes, D. St. Johnston, Current Biology 7, 468–478, Jun. 11, 1997.

"The Mammalian Homologue of *mago nashi* Encodes a Serum–Inducible Protein"; X.F. Zhao, T. Colaizzo–Anas, N.J. Nowak, T.B. Shows, R. W. Elliott, P.D. Aplan, Genomics 47, 319–322, 1998.

"*Mag–1*, a Homolog of *Drosophila mago nashi*, Regulates Hermaphrodite Germ–Line Sex Determination in *Caenorhabditis elegans*"; W. Li, R. Boswell, W.B. Wood, Developmental Biology 218, 172–182, 2000.

"Magoh Interacts with a Novel RNA–Binding Protein"; X.F. Zhao, N.J. Nowak, T.B. Shows, P.D. Aplan, Genomics 63, 145–148, 2000.

* cited by examiner

*Primary Examiner*—Karen Cochrane Carlson
(74) *Attorney, Agent, or Firm*—Womble Carlyle Sandridge & Rice, PLLC

(57) ABSTRACT

The present invention relates to isolated or non-natural nucleic acids encoding at least a portion of an avian *Mago* protein or a variant thereof. Nucleic acids comprising all or part of the *Mago nashi*-encoding region and/or an untranslated region of a *Mago nashi* cDNA are used as probes for hybridizing and detecting nucleic acids encoding all or part of a *Mago* protein. Recombinant cells, tissues and animals containing recombinant nucleic acids including expression vectors and encoding *Mago*, antibodies to the *Mago* proteins, assays utilizing the *Mago* polypeptide are within the scope of the present invention. Recombinant nucleic acid molecules may contain transcription regulatory sequences, a sequence complementary to a mRNA sequence encoding a *Mago*-related polypeptide and transcriptional control sequences functional in a recipient cell. Oligopeptides having amino acid sequences derived from the avian *Mago* protein may be used to induce the formation of polyclonal or monoclonal antibodies that specifically bind to the chicken *Mago* protein.

20 Claims, 3 Drawing Sheets

Fig. 1

```
GGGTGCGGCGCGGCGGGACCATGGCGAGCGACTTCTACCTGCGCTACTACGTGGGGCACA
AGGGGAAATTCGGGCACGAGTTCTGGAGTTCGAGTTCCGGCCCGACGGGAAGCTGCGCTA
CGCCAACAACAGCAACTACAAGAACGACGTCATGATCCGCAAAGAGGCCTACGTGCACAA
GAGCGTGATGGAGGAGCTGAAGCGGATCATCGACGACAGCGAGATCACCAAAGAGGACGA
TGCGCTGTGGCCGCCACCAGACAGGGTGGGCCGCCAGGAGCTTGAAATAGTAATTGGTGA
CGAGCACATCTCCTTTACCACGTCAAAAATTGGGTCGCTCATCGATGTAAATCAATCCAA
GGATCCAGAAGGTTTGAGAGTGTTCTACTACCTGGTCCACGACCTTAAATGTCTAGTCTT
CAGTCTTATTGGACTACACTTCAAGATTAAGCCAATCTAAATCAAACAAACTGAAGTTTG
TACTGCAGTGTCTGTACATGAGGGGGGGCATGCTTTTTCAATTCCTTGCTTCTTCAGACC
CGAAACTTTTATGTATGTTAGAATTCTTTTTACAAACTGTAAGTGACTGTCTTAATAAAA
TGTTGACATGGGGTATTTTAACTTGGAAAAAAAAAAAAAAAAAA
```

Fig.2

MASDFYLRYYVGHKGKFGHEFLEFEFRPDGKLRYANNSNYKNDVMIRKEAYVHKSVMEEL
KRIIDDSEITKEDDALWPPPDRVGRQELEIVIGDEHISFTTSKTGSLIDVNQSKDPEGLR
VFYYLVQDLKCLVFSLIGLHFKIKPI

Fig. 3

| | | |
|---|---|---|
| G. gallus | 1 | M ASDFYLRYYVGHKGKFGHEFLEFEFRPDGKLRYANNSNYKNDVMIRKEAYVHKSVMEE |
| X. laevis | 1 | M GSDFYLRYYVGHKGKFGHEFLEFEFRPDGKLRYRANNSNYKNDVMIRKEAYVHKSVMEE |
| H. sapiens | 1 | M ESDFYLRYYVGHKGKFGHEFLEFEFRPDGKLRYANNSNYKNDVMIRKEAYVHKSVMEE |
| M. musculus | 1 | M ESDFYLRYYVGHKGKFGHEFLEFEFRPDGKLRYANNSNYKNDVMIRKEAYVHKSVMEE |
| D. melanogaster | 1 | MSTEDFYLRYYVGHKGKFGHEFLEFEFRPDGKLRYANNSNYKNDTMIRKEAFVHQSVMEE |

| | | |
|---|---|---|
| G. gallus | 61 | LKRIIDDSEITKEDDALWPPPDRVGRQELEIVIGDEHISFTTSKTGSLIDVNQSKDPEGL |
| X. laevis | 61 | LKRIIDDSEVTKEDDALWPPPDRVGRQELEIVIGDEHISFTTSKTGSLIDVNQSKDPEGL |
| H. sapiens | 61 | LKRIIDDSEITKEDDALWPPPDRVGRQELEIVIGDEHISFTTSKTGSLIDVNQSKDPEGL |
| M. musculus | 61 | LKRIIDDSEITKEDDALWPPPDRVGRQELEIVIGDEHISFTTSKTGSLIDVNQSKDPEGL |
| D. melanogaster | 62 | LKRIIDSEIMQEDDLPWPPDRVGRQELEIVIGDEHISFTTSKTGSLVDVNRSKDPEGL |

| | | |
|---|---|---|
| G. gallus | 121 | RVFYLVQDLKCLVFSLIGLHFKIKPI 146 |
| X. laevis | 121 | RVFYLVQDLKCLVESLIGLHFKIKPI 146 |
| H. sapiens | 121 | RVFYLVQDLKCLVFSLIGLHFKIKPI 146 |
| M. musculus | 121 | RVFYLVQDLKCLVFSLIGLHFKIKPI 146 |
| D. melanogaster | 122 | RCFYLVQDLKCLVFSLIGLHFKIKPI 147 |

SEQUENCE LISTING

<160> NUMBER OF SEQ ID NOS: 9

<210> SEQ ID NO 1
<211> LENGTH: 644
<212> TYPE: DNA
<213> ORGANISM: Gallus gallus

<400> SEQUENCE: 1

```
gggtgcggcg cggcgggacc atggcgagcg acttctacct gcgctactac gtggggcaca      60
aggggaaatt cgggcacgag ttctggagtt cgagttccgg cccgacggga agctgcgcta     120
cgccaacaac agcaactaca agaacgacgt catgatccgc aaagaggcct acgtgcacaa     180
gagcgtgatg gaggagctga agcggatcat cgacgcagc gagatcacca aagaggacga     240
tgcgctgtgg ccgccaccag acagggtggg ccgccaggag cttgaaatag taattggtga     300
cgagcacatc tcctttacca cgtcaaaaat tgggtcgctc atcgatgtaa atcaatccaa     360
ggatccagaa ggtttgagag tgttctacta cctggtccac gaccttaaat gtctagtctt     420
cagtcttatt ggactacact tcaagattaa gccaatctaa atcaaacaaa ctgaagtttg     480
tactgcagtg tctgtacatg agggggggca tgcttttca attccttgct tcttcagacc      540
cgaaactttt atgtatgtta gaattctttt tacaaactgt aagtgactgt cttaataaaa     600
tgttgacatg gggtatttta acttggaaaa aaaaaaaaaa aaaa                      644
```

<210> SEQ ID NO 2
<211> LENGTH: 146
<212> TYPE: PRT
<213> ORGANISM: Gallus gallus

<400> SEQUENCE: 2

```
Met Ala Ser Asp Phe Tyr Leu Arg Tyr Tyr Val Gly His Lys Gly Lys
1               5                   10                  15

Phe Gly His Glu Phe Leu Glu Phe Glu Phe Arg Pro Asp Gly Lys Leu
            20                  25                  30

Arg Tyr Ala Asn Asn Ser Asn Tyr Lys Asn Asp Val Met Ile Arg Lys
        35                  40                  45

Glu Ala Tyr Val His Lys Ser Val Met Glu Glu Leu Lys Arg Ile Ile
    50                  55                  60

Asp Asp Ser Glu Ile Thr Lys Glu Asp Asp Ala Leu Trp Pro Pro Pro
65                  70                  75                  80

Asp Arg Val Gly Arg Gln Glu Leu Glu Ile Val Ile Gly Asp Glu His
                85                  90                  95

Ile Ser Phe Thr Thr Ser Lys Thr Gly Ser Leu Ile Asp Val Asn Gln
            100                 105                 110

Ser Lys Asp Pro Glu Gly Leu Arg Val Phe Tyr Tyr Leu Val Gln Asp
        115                 120                 125

Leu Lys Cys Leu Val Phe Ser Leu Ile Gly Leu His Phe Lys Ile Lys
    130                 135                 140

Pro Ile
145
```

<210> SEQ ID NO 3
<211> LENGTH: 18
<212> TYPE: DNA
<213> ORGANISM: Gallus gallus

<400> SEQUENCE: 3

```
tccgagatct ggacgagc                                                      18

<210> SEQ ID NO 4
<211> LENGTH: 20
<212> TYPE: DNA
<213> ORGANISM: Gallus gallus

<400> SEQUENCE: 4
ccctatagtg agtcgtatta                                                    20

<210> SEQ ID NO 5
<211> LENGTH: 26
<212> TYPE: DNA
<213> ORGANISM: Gallus gallus

<400> SEQUENCE: 5
ctcgggaagc gcgccattgt gttggt                                             26

<210> SEQ ID NO 6
<211> LENGTH: 146
<212> TYPE: PRT
<213> ORGANISM: Xenopus laevis

<400> SEQUENCE: 6
```

Met Gly Ser Asp Phe Tyr Leu Arg Tyr Tyr Val Gly His Lys Gly Lys
1               5                   10                  15

Phe Gly His Glu Phe Leu Glu Phe Glu Phe Arg Pro Asp Gly Lys Leu
            20                  25                  30

Tyr Arg Ala Asn Asn Ser Asn Tyr Lys Asn Asp Val Met Ile Arg Lys
        35                  40                  45

Glu Ala Tyr Val His Lys Ser Val Met Glu Glu Leu Lys Arg Ile Ile
    50                  55                  60

Asp Asp Ser Glu Val Thr Lys Glu Asp Ala Leu Trp Pro Pro Pro
65                  70                  75                  80

Asp Arg Val Gly Arg Gln Glu Leu Glu Ile Val Ile Gly Asp Glu His
                85                  90                  95

Ile Ser Phe Thr Thr Ser Lys Thr Gly Ser Leu Ile Asp Val Asn Gln
            100                 105                 110

Ser Lys Asp Pro Glu Gly Leu Arg Val Phe Tyr Tyr Leu Val Gln Asp
        115                 120                 125

Leu Lys Cys Leu Val Glu Ser Leu Ile Gly Leu His Phe Lys Ile Lys
    130                 135                 140

Pro Ile
145

```
<210> SEQ ID NO 7
<211> LENGTH: 146
<212> TYPE: PRT
<213> ORGANISM: Homo sapiens

<400> SEQUENCE: 7
```

Met Glu Ser Asp Phe Tyr Leu Arg Tyr Tyr Val Gly His Lys Gly Lys
1               5                   10                  15

Phe Gly His Glu Phe Leu Glu Phe Glu Phe Arg Pro Asp Gly Lys Leu
            20                  25                  30

Arg Tyr Ala Asn Asn Ser Asn Tyr Lys Asn Asp Val Met Ile Arg Lys
        35                  40                  45

Glu Ala Tyr Val His Lys Ser Val Met Glu Glu Leu Lys Arg Ile Ile

```
                    50                  55                  60
Asp Asp Ser Glu Ile Thr Lys Glu Asp Ala Leu Trp Pro Pro
 65                  70                  75                  80

Asp Arg Val Gly Arg Gln Glu Leu Glu Ile Val Ile Gly Asp Glu His
                 85                  90                  95

Ile Ser Phe Thr Thr Ser Lys Thr Gly Ser Leu Ile Asp Val Asn Gln
                100                 105                 110

Ser Lys Asp Pro Glu Gly Leu Arg Val Phe Tyr Tyr Leu Val Gln Asp
            115                 120                 125

Leu Lys Cys Leu Val Phe Ser Leu Ile Gly Leu His Phe Lys Ile Lys
        130                 135                 140

Pro Ile
145

<210> SEQ ID NO 8
<211> LENGTH: 146
<212> TYPE: PRT
<213> ORGANISM: Mus musculus

<400> SEQUENCE: 8

Met Glu Ser Asp Phe Tyr Leu Arg Tyr Tyr Val Gly His Lys Gly Lys
  1               5                  10                  15

Phe Gly His Glu Phe Leu Glu Phe Glu Phe Arg Pro Asp Gly Lys Leu
                 20                  25                  30

Arg Tyr Ala Asn Asn Ser Asn Tyr Lys Asn Asp Val Met Ile Arg Lys
             35                  40                  45

Glu Ala Tyr Val His Lys Ser Val Met Glu Glu Leu Lys Arg Ile Ile
 50                  55                  60

Asp Asp Ser Glu Ile Thr Lys Glu Asp Ala Leu Trp Pro Pro
 65                  70                  75                  80

Asp Arg Val Gly Arg Gln Glu Leu Glu Ile Val Ile Gly Asp Glu His
                 85                  90                  95

Ile Ser Phe Thr Thr Ser Lys Thr Gly Ser Leu Ile Asp Val Asn Gln
                100                 105                 110

Ser Lys Asp Pro Glu Gly Leu Arg Val Phe Tyr Tyr Leu Val Gln Asp
            115                 120                 125

Leu Lys Cys Leu Val Phe Ser Leu Ile Gly Leu His Phe Lys Ile Lys
        130                 135                 140

Pro Ile
145

<210> SEQ ID NO 9
<211> LENGTH: 147
<212> TYPE: PRT
<213> ORGANISM: Drosophila melanogaster

<400> SEQUENCE: 9

Met Ser Thr Glu Asp Phe Tyr Leu Arg Tyr Tyr Val Gly His Lys Gly
  1               5                  10                  15

Lys Phe Gly His Glu Phe Leu Glu Phe Glu Phe Arg Pro Asp Gly Lys
                 20                  25                  30

Leu Arg Tyr Ala Asn Asn Ser Asn Tyr Lys Asn Asp Thr Met Ile Arg
             35                  40                  45

Lys Glu Ala Phe Val His Gln Ser Val Met Glu Glu Leu Lys Arg Ile
 50                  55                  60

Ile Ile Asp Ser Glu Ile Met Gln Glu Asp Asp Leu Pro Trp Pro Pro
```

-continued

```
            65                  70                  75                  80
Pro Asp Arg Val Gly Arg Gln Glu Leu Glu Ile Val Ile Gly Asp Glu
                    85                  90                  95

His Ile Ser Phe Thr Thr Ser Lys Thr Gly Ser Leu Val Asp Val Asn
                100                 105                 110

Arg Ser Lys Asp Pro Glu Gly Leu Arg Cys Phe Tyr Tyr Leu Val Gln
            115                 120                 125

Asp Leu Lys Cys Leu Val Phe Ser Leu Ile Gly Leu His Phe Lys Ile
        130                 135                 140

Lys Pro Ile
145
```

AVIAN *MAGO NASHI* GENE

FIELD OF THE INVENTION

The present invention relates generally to the identification of an avian *Mago nashi* gene, specifically from chicken, and to the corresponding protein and coding sequences thereof. More specifically, the invention relates to a nucleotide sequence encoding the chicken *Mago* protein, and to methods and compositions that employ this coding sequence, for the regulation of the gender in avian species.

BACKGROUND

The ability to manipulate the sex determination pathways during embryonic development so as to favor one sex or the other can have significant economic benefits for the poultry industry. For layer breeders who focus on hens for egg production, the conversion from males to females is of particular concern. Typically, new-born chicks are screened by hand and up to 98% of the males are destroyed. The remaining 2% of males are retained for breeding purposes. Wastage of new-borns and the labor costs of saving the birds are, therefore, a major financial burden. Conversely, broiler production requires predominantly male birds in the flocks because of the 10–15% body weight advantage of male birds compared to female birds.

There is a significant economic incentive, therefore, to identify genes that regulate germ-line development and thereby be used to direct the gender distribution of birds. For example, altering the level of suppression of such a gene in a transgenic animal could drive an embryo down the male or female path.

The gene *Mago nashi* (grandchildless) was first identified in the fruit fly *Drosophila melanogaster*, and shown to be involved in the localization and development of germ cells. See Boswell et al., Development 113, 373–384 (1991). In *Drosophila*, the *Mago* gene product is necessary for anterior-posterior polarization in the oocyte. (Newmark et al., Development 124, 3197–3207 (1997)). The *Mago nashi* gene is also required for the continued viability of the *Drosophila* embryo and the dorsal-ventral migration of the oocyte nucleus to the anteriodorsal position (Newmark et al., Development 124, 3197–3207 (1997)).

Highly conserved homologs of the *Drosophila Mago nashi* gene are widespread throughout the animal kingdom and in plants, but are not found in fungi or bacteria (Micklem et al., Current Biol. 7, 468–478 (1997)). In animals, *Mago*-related amino acid sequences have been isolated from *Caenorhabditis elegans, Xenopus laevis, Mus musculus* (mouse) (Newmark et al., Development 124, 3197–3207 (1997)) and human (Zhao et al., Genomics 47, 319–322 (1998)). In *Drosophila*, the protein product of *Mago nashi* is a 147 amino acid (aa) protein. The human homolog MAGOH is a 146-aa protein, the sequence of which has 90% identity to the *Drosophila* equivalent. While the mouse MAGOH amino acid sequence is the same as the human MAGOH sequence, the nucleotide sequence is only 88% identical (Zhao et al., Genomics 47, 319–322 (1998)). The mammalian MAGOH and *C. elegans Mago nashi* homolog are only 77% similar in amino acid sequence.

Although the highly conserved mammalian MAGOH proteins display sequence variation when compared to the invertebrate homologs, two regions of the protein are conserved and identical in all species examined. An N-region conserved domain is also found in a related (but partial) amino acid sequence obtained from rice (*Oryza sativa*) (Zhao et al., Genomics 47, 319–322 (1998)). The overall conservation of the protein, and absolute preservation of the sequence in two domains probably reflects that the *Mago* protein has central functions key to the survivability of multicellular organisims.

While the activity of the *D. melangogaster Mago nashi* gene product has been shown as necessary for germ-line development, in humans the MAGOH gene is expressed in all tissues, both adult and fetal, that have proliferating cells. MAGOH is serum inducible in quiescent cells supporting its role in cell proliferation and interacts with an RNA-binding protein (Zhao et al., Genomics 63, 145–148 (2000)).

The role of the MAGOH gene or its homologs in cell development is ill-defined. In *Drosophila*, at least, it is involved in oogenesis. In humans, it is at high levels in proliferating cells. In *C. elegans*, however, the mag-1 gene, the homolog of *Mago nashi*, regulates masculanization of the hermaphrodite germ-line (Li et al, Develop. Biol. 218, 172–182 (2000)). Thus, RNA-mediated interference of mag-1 caused masculanization of *C. elegans* hermaphrodite, and it has been suggested that mag-1 functions by inhibiting one or more genes participating in masculanization.

The part played by the *C. elegans* mag-1 gene in determining the sexual development of the worm, and the highly conserved nature of the protein, signifies the importance of identifying the *Mago nashi* gene, and the expressed product thereof, from the chicken. The identification and isolation of the chicken *Mago nashi* gene will enable detection of the gene products, including RNA transcripts and protein products, in the various tissues of chicken. Furthermore, isolated *Mago nashi*-related nucleic acids will enable the manipulation of *Mago nashi* gene activity so that the gender of a chicken may be selected in favor one sex or the other. Thus, directing the production of either males or females will be to the economic advantage of poultry breeders and allow the successful generation of stable transgenic populations of birds. The similarity of the *Mago* homologs will enable this technology to be applied to other avian populations yielding economic or conservation benefits.

SUMMARY OF THE INVENTION

Briefly described, the present invention relates to a novel avian protein called *Mago* and nucleolide sequences that encode it.

One aspect of the present invention relates to isolated or non-naturally occurring nucleic acid molecules that encode at least a portion of an avian *Mago* protein or a variant thereof.

The present invention provides isolated molecules that can hybridize to nucleic acid sequences of the genome of a bird and which encode the *Mago* protein or variants thereof.

The present invention further provides nucleic acids that are fragments or derivatives of the cDNA molecules comprising at least in part a region of the *Mago nashi* coding region and or an untranslated region of the cDNA, wherein the fragments may be used as probes specific for hybridizing and detecting nucleic acid molecules that encode at least in part a region of the *Mago* protein.

Also within the scope of the present invention are recombinant cells, tissues and animals containing non-naturally occurring recombinant nucleic acid molecules encoding *Mago*, including expression vectors for the expression of the *Mago nashi* gene, antibodies to the *Mago* proteins, assays utilizing the *Mago* polypeptide, and methods relating to all of the foregoing. Also within the scope of the present invention is the development of therapeutic and diagnostic agents that mimic, facilitate or inhibit the action of *Mago*, and/or are based on relationships to the structure and action of *Mago*.

The invention further provides non-naturally occurring recombinant nucleic acid molecules encoding *Mago* that can be in a cell or an organism. The recombinant nucleic acid may comprise *Mago nashi*-related sequences, functional derivatives thereof, and a vector or a promoter effective to initiate transcription in a host cell. The recombinant nucleic acid molecule can alternatively contain transcription regulatory sequences functional in a particular cell, a sequence complementary to a mRNA sequence encoding a *Mago*-related polypeptide and transcriptional control sequences functional in that cell.

The present invention still further provides oligopeptides having amino acid sequences derived from the amino acid sequence of an avian *Mago* protein that may be used to induce the formation of polyclonal or monoclonal antibodies that specifically bind to at least one region of the chicken *Mago* protein. The antibodies may be used for, but are not limited to, the detection and assay of *Mago* in biological samples, or the purification of the *Mago* protein. Diagnostic kits for the detection of *Mago* in biological samples are also within the scope of the present invention.

The invention features methods for identifying vertebrate cells containing an avian *Mago* polypeptide, or a related sequence thereof. Such methods comprise identifying the *Mago* polypeptide in mammalian cells using techniques that are routine and standard in the art, for example, PCR amplification, and Northern, Western, Southern and Southwestern blotting using oligonucleotides and derivatives thereof, or antibodies specific to the *Mago* protein.

Additional objects and aspects of the present invention will become more apparent upon review of the detailed description set forth below when taken in conjunction with the accompanying figures, which are briefly described as follows.

BRIEF DESCRIPTION OF THE FIGURES

FIG. 1 illustrates the nucleotide sequence (SEQ ID NO: 1) of one cDNA clone isolated from a cDNA library constructed from 7-day-old chick embryos and encoding the chicken *Mago* polypeptide (SEQ ID NO: 2).

FIG. 2 illustrates the predicted amino acid sequence (SEQ ID NO: 2) of the chicken *Mago* homolog of *Drosophila Mago nashi*, and the human and mouse MAGOH.

FIG. 3 illustrates the alignment of the sequences of the proteins encoded by the *Mago nashi* of several species, including the chicken *Mago nashi* gene (SEQ ID NO: 1).

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

This description uses gene nomenclature accepted by the Cucurbit Genetics Cooperative as it appears in the *Cucurbit Genetics Cooperative Report* 18:85 (1995); herein incorporated by reference in its entirety. Using this gene nomenclature, genes are symbolized by italicized Roman letters. If a mutant gene is recessive to the normal type, then the symbol and name of the mutant gene appear in italicized lower case letters.

For convenience, certain terms employed in the specification, examples, and appended claims are collected here.

Definitions

The term "animal" is used herein to include all vertebrate animals, including humans. It also includes an individual animal in all stages of development, including embryonic and fetal stages.

The term "avian" as used herein refers to any species, subspecies or race of organism of the taxonomic class ava, such as, but not limited to, such organisms as chicken, turkey, duck, goose, quail, pheasants, parrots, finches, hawks, crows and ratites including ostrich, emu and cassowary.

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes a *Mago* protein or a variant thereof of the present invention.

By the use of the term "enriched" in reference to nucleic acid it is meant that the specific DNA or RNA sequence constitutes a significantly higher fraction of the total DNA or RNA present in the cells or solution of interest than in normal or diseased cells or in the cells from which the sequence was taken. Enriched does not imply that there are no other DNA or RNA sequences present, just that the relative amount of the sequence of interest has been significantly increased. The other DNA may, for example, be derived from a yeast or bacterial genome, or a cloning vector, such as a plasmid or a viral vector. The term significant as used herein is used to indicate that the level of increase is useful to the person making such an increase.

It is advantageous for some purposes that a nucleotide sequence is in purified form. The term "purified" in reference to nucleic acid represents that the sequence has increased purity relative to the natural environment.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology, isolated from an appropriate source such as a bird, or are synthesized. The term "polypeptides" further contemplates polypeptides as defined above that include chemically modified amino acids or amino acids covalently or noncovalently linked to labeling ligands.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "modulates" as used herein refers to the ability of a compound to alter the function of a *Mago* protein. A modulator preferably increases the binding or biological activity potential of a *Mago*. A modulator can alternatively decrease the binding or biological activity potential of the *Mago* polypeptide or fragments thereof.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes", "heterologous genes" or "exogenous genes" and genes that are naturally a part of a particular organism's genome are referred to as "endogenous genes". The term "knock-out" refers to a procedure by which an endogenous gene is made non-functional. In a similar manner, the term "knock-in" refers to a procedure by which an exogenous gene is integrated into a target animal's genome. The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and which, therefore, are not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein or polypeptide or a portion thereof.

As used herein, the term "locus" or "loci" refers to the site of a gene on a chromosome. Pairs of genes control hereditary traits, each in the same position on a pair of chromosomes. These gene pairs, or alleles, may both be dominant or both be recessive in expression of that trait. In either case, the individual is said to be homozygous for the trait controlled by that gene pair. If the gene pair (alleles) consists of one dominant and one recessive trait, the individual is heterozygous for the trait controlled by the gene pair. Natural variation in genes or nucleic acid molecules caused by, for example, recombination events or resulting from mutation, gives rise to allelic variants with similar, but not identical, nucleotide sequences. Such allelic variants typically encode proteins with similar activity to that of the protein encoded by the gene to which they are compared, because natural selection typically selects against variations that alter function. Allelic variants can also comprise alterations in the untranslated regions of the gene as, for example, in the 3' or 5' untranslated regions or can involve alternate splicing of a nascent transcript, resulting in alternative exons being positioned adjacently.

The term "transcription regulatory sequences" as used herein refers to nucleotide sequences that are associated with a gene nucleic acid sequence and which regulate the transcriptional expression of the gene. The "transcription regulatory sequences" may be isolated and incorporated into a vector nucleic acid to enable regulated transcription in appropriate cells of portions of the vector DNA. The "transcription regulatory sequence" may precede, but are not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "coding region" as used herein refers to a continuous linear arrangement of nucleotides that may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "probe" as used herein, when referring to a nucleic acid, refers to a nucleotide sequence that can be used to hybridize with and thereby identify the presence of a complementary sequence, or a complementary sequence differing from the probe sequence but not to a degree that prevents hybridization under the hybridization stringency conditions used. The probe may be modified with labels such as, but not only, radioactive groups, biotin, or any other label that is well known in the art.

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a *Mago* gene or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g., low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in aqueous solution, followed by washing with 1×SSC at 65° Celsius. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267–284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al (1989) Molecular Cloning: A Laboratory Manual 2nd ed. Cold Spring Harbor Press, the contents of which are herein incorporated by reference in their entirety.

The terms "unique nucleic acid region" and "unique protein (polypeptide) region" as used herein refer to sequences present in a nucleic acid or protein (polypeptide) respectively that is not present in any other nucleic acid or protein sequence. The terms "conserved nucleic acid region" as referred to herein is a nucleotide sequence present in two or more nucleic acid sequences, to which a particular nucleic acid sequence can hybridize under low, medium or high stringency conditions. The greater the degree of conservation between the conserved regions of two or more nucleic acid sequences, the higher the hybridization stringency that will allow hybridization between the conserved region and a particular nucleic acid sequence.

The terms "percent sequence identity" or "percent sequence similarity" as used herein refer to the degree of sequence identity between two nucleic acid sequences or two amino acid sequences as determined using the algorithm of Karlin & Attschul (1990) Proc. Natl. Acad. Sci. 87: 2264–2268, modified as in Karlin & Attschul (1993) Proc. Natl. Acad. Sci. 90: 5873–5877. Such an algorithm is incorporated into the NBLAST and XBLAST programs of Attschul et al. (1990) T. Mol. Biol. Q15: 403–410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Attschul et al. (1997) Nuc. Acids Res. 25: 3389–3402. When utilizing BLAST and Gapped BLAST programs, the default parameters of the respective programs (e.g., XBLAST and NBLAST) are used. See htt://www.ncbi.nlm.nih.gov.

Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "sense strand" as used herein refers to a single stranded DNA molecule from a genomic DNA that may be transcribed into RNA and translated into the natural polypeptide product of the gene. The term "antisense strand" is used herein to mean the single strand DNA molecule of a genomic DNA that is complementary with the sense strand of the gene.

The term "antisense DNA" as used herein refers to a gene sequence DNA that has a nucleotide sequence complementary to the "sense strand" of a gene when read in reverse orientation, i.e., DNA read into RNA in a 3' to 5' direction rather than in the 5' to 3' direction. The term "antisense RNA" is used to mean an RNA nucleotide sequence (for example that encoded by an antisense DNA or synthesized complementary with the antisense DNA). Antisense RNA is capable of hybridizing under stringent conditions with an antisense DNA. The antisense RNA of the invention is useful for regulating expression of a "target gene" either at the transcriptional or translational level. For example, transcription of the subject nucleic acids may produce antisense transcripts that are capable of inhibiting transcription by inhibiting initiation of transcription or by competing for limiting transcription factors; or, the antisense transcripts may inhibit transport of the "target RNA", or, the antisense transcripts may inhibit translation of "target RNA".

The term "antisense therapy" as used herein refers to the administration or in situ generation of oligonucleotide probes or their derivatives that specifically hybridize (e.g., bind) under cellular conditions, with the cellular mRNA and/or genomic DNA encoding a *Mago* protein so as to inhibit expression of that protein, e.g., by inhibiting transcription and/or translation. The binding may be by conventional base pair complementation, or, for example, in the case of binding to DNA duplexes, through specific interactions in the major groove of the double helix. In general, "antisense" therapy refers to the range of techniques generally employed in the art, and includes any therapy that relies on specific binding to oligonucleotide sequences.

The term "nucleic acid vector" as used herein refers to a natural or synthetic single or double stranded plasmid or viral nucleic acid molecule that can be transfected or transformed into cells and replicate independently of, or within, the host cell genome. A circular double stranded plasmid can be linearized by treatment with an appropriate restriction enzyme based on the nucleotide sequence of the plasmid vector. A nucleic acid can be inserted into a vector by cutting the vector with restriction enzymes and ligating the pieces together. The nucleic acid molecule can be RNA or DNA.

The term "expression vector" as used herein refers to a nucleic acid vector that may further include at least one regulatory sequence operably linked to a nucleotide sequence coding for the *Mago* protein. Regulatory sequences are well recognized in the art and may be selected to ensure good expression of the linked nucleotide sequence without undue experimentation by those skilled in the art. As used herein, the term "regulatory sequences" includes promoters, enhancers, and other elements that may control expression. Standard molecular biology textbooks such as Sambrook et al. eds "Molecular Cloning: A Laboratory Manual" 2nd ed. Cold Spring Harbor Press (1989) may be consulted to design suitable expression vectors, promoters, and other expression control elements. It should be recognized, however, that the choice of a suitable expression vector depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only a calcium or magnesium salt, an electric field, detergent, or liposome mediated transfection, to render the host cell competent for the uptake of the nucleic acid molecules.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell can harbor a vector that is extragenomic. An extragenomic nucleic acid vector does not insert into the cell's genome. A recombinant cell can further harbor a vector or a portion thereof that is intragenomic. The term intragenomic defines a nucleic acid construct incorporated within the recombinant cell's genome.

The term "recombinant nucleic acid" as used herein refers to combinations of at least two nucleic acid sequences that are not naturally found in a eukaryotic or prokaryotic cell. The nucleic acid sequences may include, but are not limited to nucleic acid vectors, gene expression regulatory elements, origins of replication, sequences that when expressed confer antibiotic resistance, and protein-encoding sequences. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "epitope" refers to a part of the protein that can specifically bind to an antibody by fitting into the antigen-binding site of the antibody.

The term "antibody" as used herein refers to polyclonal and monoclonal antibodies and fragments thereof, and immunologic binding equivalents thereof that are capable of specifically binding to the *Mago* polypeptides and fragments thereof, including epitopes thereof. The term "antibody" refers to a homogeneous molecular entity, or a mixture such as a serum product made up of a plurality of different molecular entities, and may further comprise any modified or derivatised variant thereof that retains the ability to specifically bind to *Mago*-related polypeptides.

Described herein are methods for the production of antibodies capable of specifically recognizing one or more differentially expressed or pathway gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a fingerprint, target, or pathway gene in a biological sample, or, alternatively, as a method for the inhibition of abnormal target gene activity.

For the production of antibodies to a differentially expressed or pathway gene, various host animals may be immunized by injection with a differentially expressed or pathway gene protein, or a portion thereof. Such host animals may include but are not limited to rabbits, mice, and rats, to name but a few. Various adjuvants may be used to increase the immunologic response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a target gene product, or an antigenic functional derivative thereof. For the production of polyclonal antibodies, host animals such as those described above, may be immunized by injection with differentially expressed or pathway gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of Kohler & Milstein (1975) Nature 256: 495–497; and U.S. Pat. No. 4,376,110; the human B-cell hybridoma technique (Kosbor et al. (1983) Immunology Today 4: 72; Cole et al. (1983) Proc. Natl. Acad. Sci. 80: 2026–2030), and the EBV-hybridoma technique (Cole et al. (1985) Monoclonal Antibodies And Cancer Therapy Alan R. Liss, Inc. pp. 77–96). Briefly, spleen cells are harvested from an immunized mouse and fused with immortalizing cells (i.e., myeloma cells) to yield antibody-producing hybridomas. Hybridomas can be screened immunochemically for the production of monoclonal antibodies specifically reactive with the *Mago* protein.

Protocols for producing, isolating and purifying conventional and monoclonal antibodies may be analogous to those described in Cassone et al. (1988) J. Med. Microbiol. 27: 233–238; Hancock & Evan Production and Characterization of Antibodies against Synthetic Peptides pp23–33 in Immunochemical Protocols ed. M. M. Manson, (1992) (Humana Press, Totowa, N.J.); Goding, J. W., Monoclonal Antibodies: Principles and Practice, 2d ed., (1986) (Academic Press Ltd., London) and Lam & Mutharia, "Antigen-Antibody Reactions," pp104–132 in Methods for General and Molecular Bacteriology, ed. P. Gerhardt, (1994) (ASM Press, Washington, D.C.) the contents of which are incorporated herein by reference in their entirety. Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al. (1984) Proc. Natl. Acad. Sci. 81: 6851–6855; Neuberger et al. (1984) Nature 312: 604–608; Takeda et al. (1985) Nature 314: 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies such as, but not only U.S. Pat. No. 4,946,778; Bird (1988) Science 242: 423–426; Huston et al. (1988) Proc. Natl. Acad. Sci. 85: 5879–5883; and Ward et al. (1989) Nature 334: 544–546 can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to, the F(ab')$_2$ fragments that can be produced by pepsin digestion of the antibody molecule and the Fab fragments which can be generated by reducing the disulfide bridges of the F(ab')$_2$ fragments. Alternatively, Fab expression libraries may be constructed (Huse et al. (1989) Science 246: 1275–1281) to allow rapid and easy identification of monoclonal Fab fragments with the desired specificity.

Pharmaceutical compositions comprising agents that will modulate the physiological activity of the *Mago* gene product or the regulation of the expression of the *Mago nashi* gene can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Pharmaceutical compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Pharmaceutical compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remmington's Pharmaceutical Science," 17th edition, 1985 may be consulted to prepare suitable preparations, without undue experimentation. Dosages can generally range from a few hundred milligrams to a few grams.

As used herein, a "transgenic animal" is any animal, preferably an avian species, in which one or more of the cells of the bird contain heterologous nucleic acid introduced by way of human intervention, such as by transgenic techniques well known in the art. The nucleic acid is introduced into a cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animal, the transgene causes cells to express a recombinant form of the subject *Mago* protein, e.g., either agonistic or antagonistic forms, or in which the endogenous *Mago nashi* gene has been disrupted. However, transgenic animals in which the recombinant *Mago nashi* gene is silent are also contemplated, as for example, the FLP or CRE recombinase dependent constructs described below. The terms "chimeric animal" or "mosaic animal" are used herein to refer to animals in which the recombinant gene is found, or in which the recombinant is expressed in some but not all cells of the animal. The term "tissue-specific chimeric animal" indicates that the recombinant *Mago nashi* gene is present and/or expressed in some tissues but not others.

As used herein, the term "transgene" means a nucleic acid sequence (encoding, for example, a *Mago* polypeptide) that is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The techniques used to isolate and characterize the nucleic acids and proteins of the present invention are well known to those of skill in the art and standard molecular biology and biochemical manuals may be consulted to select suitable protocols without undue experimentation. See, for example, Sambrook et al (1989) Molecular Cloning: A Laboratory Manual 2nd ed. Cold Spring Harbor Press, the content of which is herein incorporated by reference in its entirety.

Abbreviations

Abbreviations used in the present specification include the following: aa, amino acid(s); bp, base pair(s); cDNA, DNA complementary to RNA; nt, nucleotide(s); SSC, sodium chloride-sodium citrate; DMSO, dimethyl sulfoxide.

The present invention provides isolated nucleic acids, derivatives and variants thereof that encode an avian *Mago* protein, derivative, variant or fragment thereof.

The present invention provides for the use of an isolated cDNA as a probe to screen a chicken-derived cDNA library to obtain isolated nucleic acids capable of hybridizing with the probe, as discussed in Example 1. The minimal size of a nucleic acid molecule of the present invention is a size sufficient to allow the formation of a stable hybridization product with the complementary sequence of another nucleic acid molecule under selected stringency conditions.

Chicken *Mago Nashi* Nucleic Acid Sequences

One aspect of the invention provides nucleic acids that hybridize under high, medium or low stringency conditions to a nucleic acid that encodes a peptide having all, a derivative of, or a portion of an amino acid sequence derived from the nucleic acid sequences SEQ ID NO: 1, shown in FIG. 1 (GenBank Accession No. 383945). The *Mago* protein amino acid sequence SEQ ID NO: 2, as derived from SEQ ID NO: 1 is illustrated in FIG. 2.

Isolated nucleic acids that differ in sequence from the nucleotide sequence represented in SEQ ID NO: 1 due to degeneracy in the genetic code are also within the scope of the invention. Such nucleic acids can encode functionally equivalent peptides (i.e., a polypeptide having a biological activity of a *Mago* protein) but differ in sequence from the sequence shown in SEQ ID NO: 2 shown in FIG. 2, due to degeneracy in the genetic code. Isolated nucleic acid sequence variants may also encode non-functional polypeptides, the sequences of which are substantially similar, but not identical, those of functional variants of *Mago*. These isolated nucleic acids may be used to generate variant animals with inactive or functionally modified *Mago* polypeptides or fragments, variants or derivatives thereof.

For example, a number of amino acids are designated by more than one triplet. Codons that specify the same amino acid, or synonyms (for example, CAU and CAC are synonyms for histidine) may result in "silent" mutations which do not affect the amino acid sequence of the subject protein. However, it is expected that DNA sequence polymorphisms that do lead to changes in the amino acid sequences of the present *Mago* protein of the present invention will exist from one chicken subject to the next. One skilled in the art will appreciate that these variations in one or more nucleotides (up to about 3–4% of the nucleotides) of the nucleic acids encoding peptides having an activity of, for example, a *Mago* protein may exist among individuals due to natural allelic variation. Any and all such nucleotide variations and resulting amino acid polymorphisms are within the scope of this invention.

Fragments of a nucleic acid encoding an active portion of the subject *Mago* protein are also within the scope of the invention. As used herein, a fragment of the nucleic acid encoding an active portion of a *Mago* protein refers to a nucleotide sequence having fewer nucleotides than the nucleotide sequence encoding the entire amino acid sequence of the protein but which encodes a peptide that possesses agonistic or antagonistic activity relative to a naturally occurring form of the protein.

Nucleic acid fragments within the scope of the invention also include those capable of hybridizing under high or low stringency conditions with nucleic acids from other species for use in screening protocols to detect *Mago* homologs. Comparison of the nucleic acid sequences of encoding *Mago* from various species show that oligonucleotide primers can be generated that are suitable for detecting and isolating *Mago* clones derived from other eukaryotes.

The nucleic acid molecules of the present invention can include an isolated deletion mutation corresponding to the *Mago* phenotype, a natural *Mago nashi* gene, a *Mago nashi* cDNA molecule, a degenerate variant, a truncated form thereof, a homolog thereof or any other modified versions.

In still another embodiment of the present invention, an avian *Mago nashi* gene or nucleic acid molecule can be an allelic variant of SEQ ID NO: 1.

In one embodiment of the present invention, an isolated nucleic acid molecule of the present invention includes a nucleic acid that is at least about 75%, preferably at least about 80%, more preferably at least about 85%, even more preferably at least about 90%, still more preferably at least about 95%, and even more preferably at least about 99%, identical to a chicken-derived *Mago*-encoding nucleic acid molecule as depicted in SEQ ID NO: 1.

The nucleic acid sequence of a chicken *Mago nashi* nucleic acid molecules (SEQ ID NO: 1) of the present invention allows one skilled in the art to, for example, (a) make copies of those nucleic acid molecules by procedures such as, but not limited to, insertion into a cell for replication by the cell, by chemical synthesis or by procedures such as PCR or LCR, (b) obtain nucleic acid molecules which include at least a portion of such nucleic acid molecules, including full-length genes, full-length coding regions, regulatory control sequences, truncated coding regions and the like, (c) obtain *Mago nashi* nucleic acid homologs in other avian species such as, but not limited to, turkey, duck, goose, quail, pheasant, parrot, finch, ratites including ostrich, emu and cassowary and, (d) to obtain isolated nucleic acids capable of hybridizing to an avian *Mago nashi* nucleic acid and be used to detect the presence of *Mago nashi* nucleic acid-related sequences by complementation between the probe and the target nucleic acid.

Such nucleic acid homologs can be obtained in a variety of ways including by screening appropriate expression libraries with antibodies of the present invention; using traditional cloning techniques to screen appropriate libraries; amplifying appropriate libraries or DNA using oligonucleotide primers of the present invention in a polymerase chain reaction or other amplification method; and screening public and/or private databases containing genetic sequences using nucleic acid molecules of the present invention to identify targets. Examples of preferred libraries to screen, or from which to amplify nucleic acid molecules, include but are not limited to mammalian BAC libraries, genomic DNA libraries, and cDNA libraries. Similarly, preferred sequence databases useful for screening to identify sequences in other species homologous to chicken *Mago nashi* include, but are not limited to, GenBank and the mammalian Gene Index database of The Institute of Genomics Research (TIGR).

Chicken *Mago* Protein and Derivatives

Another aspect of the present invention is to provide protein sequences that comprise an avian *Mago* protein, and derivatives and fragments thereof. One embodiment of the present invention, therefore, comprises a protein sequence (SEQ ID NO: 2, as in FIG. 2) encoded by the chicken cDNA clone nucleic acid sequence (SEQ ID NO: 1; as shown in FIG. 1).

In embodiments of the present invention, peptide fragments of a chicken *Mago* protein are provided, wherein the fragments may be immunogenic peptides, capable of inducing an immune response when administered to an animal, and which will be recognized and bound by an antibody or not immunogenic when administered to an animal.

In another embodiment of the present invention, a *Mago nashi* nucleic acid molecule of the present invention encodes a protein having an amino acid sequence that is at least about 75%, preferably at least about 80%, more preferably at least about 85%, even more preferably at least about 90%, and more preferably still at least about 95% and yet more preferably at least about 99% identical to a chicken *Mago* protein whose amino acid sequence is disclosed in SEQ ID NO: 2, as well as allelic variants of a *Mago nashi* nucleic acid molecule encoding protein variants of SEQ ID NO: 2, including nucleic acid molecules that have been modified to accommodate codon usage properties of the cells in which such nucleic acid molecules are to be expressed.

Isolated peptidyl portions of the subject *Mago* proteins within the scope of the present invention can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, one of the subject *Mago* proteins may be arbitrarily divided into fragments of desired length with no overlap of the fragments, or preferably divided into overlapping fragments of a desired length. The fragments can be produced recombinantly or by chemical synthesis.

Furthermore, it is also possible to modify the structure of a *Mago* polypeptide for such purposes as enhancing physiological efficacy, or stability (e.g., shelf life ex vivo and resistance to proteolytic degradation in vivo). Such modified peptides are considered functional equivalents of peptides having an activity of, or which antagonize, a *Mago* protein as defined herein. A modified polypeptide can be produced in which the amino acid sequence has been altered, such as by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed, Ed. by L. Stryer, W H Freeman and Co.:1981). Peptides in which more than one replacement has taken place can readily be tested in the same manner.

In one embodiment of the present invention, therefore, a host cell is transformed with a nucleic acid comprising the sequence SEQ ID NO: 1, or a variant thereof. The transformed cell may, but not necessarily, express the transformed nucleic acid to yield chicken *Mago*-derived polypeptides, or a fragment or derivative thereof.

The protein of the present invention may be produced in purified form by any known conventional techniques. For example, chicken cells may be homogenized and centrifuged. The supernatant is then subjected to sequential ammonium sulfate precipitation and heat treatment. The fraction containing the protein of the present invention is subjected to gel filtration in an appropriately sized dextran or polyacrylamide column to separate the proteins. If necessary, the protein fraction may be further purified by HPLC.

Recombinant *Mago Nashi*-Derived Nucleic Acids, and Expression Thereof

The DNA nucleic acid molecules of the present invention can be incorporated into cells using conventional recombinant DNA technology. The DNA molecule may be inserted into an expression system to which the DNA molecule is heterologous (i.e. not normally present). Alternatively, as described more fully below, the DNA molecule may be introduced into cells which normally contain the DNA molecule, as, for example, to correct a deficiency in *Mago* expression, or where over-expression of the *Mago* protein is desired.

For expression in heterologous systems, the heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen & Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

*Mago nashi*-related nucleic acid sequences, such as SEQ ID NO: 1 or a derivative or truncated variant thereof, may be introduced into viruses such as vaccinia virus. Methods for making a viral recombinant vector useful for expressing the *Mago* protein are analogous to the methods disclosed in U.S. Pat. Nos. 4,603,112; 4,769,330; 5,174,993; 5,505,941; 5,338,683; 5,494,807; 4,722,848; Paoletti, E (1996) Proc. Natl. Acad. Sci. 93: 11349–11353; Moss (1996) Proc. Natl. Acad. Sci. 93: 11341–11348; Roizman (1996) Proc. Natl. Acad. Sci. 93: 11307–11302; Frolov et al. (1996) Proc. Natl. Acad. Sci. 93: 11371–11377; Grunhaus et al. (1993) Seminars in Virology 3: 237–252 and U.S. Pat. Nos. 5,591,639; 5,589,466; and 5,580,859 relating to DNA expression vectors, inter alia; the contents of which are incorporated herein by reference in their entireties.

Recombinant viruses can also be generated by transfection of plasmids into cells infected with virus. Suitable vectors include, but are not limited to, viral vectors such as lambda vector system λgt11, λgt WES.tB, Charon 4, and plasmid vectors such as pBR322, pBR325, pACYC177, pACYC184, pUC8, pUC9, pUC18, pUC19, pLG339, pR290, pKC37, pKC11, SV 40, pBluescript II SK ± or KS ±(see "Stratagene Cloning Systems" Catalog (1993) from Stratagene, La Jolla, Calif., which is hereby incorporated by reference), pQE, pIH821, PGEX, pET series (see Studier, F. W. et. al. (1990) "Use of T7 RNA Polymerase to Direct Expression of Cloned Genes" Gene Expression Technology, vol. 185, which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al. Molecular Cloning: A Laboratory Manual, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; vertebrate cell systems infected with virus (e.g., vaccinia virus, adenovirus, etc.); insect cell systems infected with virus (e.g., baculovirus) or avian embryonic cells inoculated with the recombinant nucleic acid. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation). Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals that differ from those of eukaryotes. Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts & Lauer (1979) Methods in Enzymology 68: 473, which is hereby incorporated by reference in its entirety.

Promoters vary in their "strength" (i.e., in their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in E. coli, its bacteriophages, or plasmids, promoters such as the T7 phage promoter, lac promoter, trp promotor, recA promotor, ribosomal RNA promotor, the $P_R$ and $P_L$ promoters of coliphage lambda and others, including but not limited, to lacUV5, ompF, b/a, lpp, and the like, may be used to direct high levels of transcription of adjacent DNA segments. Additionally, a hybrid trp-lacUV5 (tac) promotor or other E. coli promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in E. coli requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the E. coli tryptophan E, D, C, B or A genes. Additionally, any SD-ATG combination produced by recombinant DNA or other techniques involving incorporation of synthetic nucleotides may be used.

Once the isolated DNA molecule of the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Recombinant expression vectors can be designed for the expression of the encoded proteins in prokaryotic or eukaryotic cells. The prokaryotic expression system may comprise the host bacterial species E. coli, B. subtilis or any other host cell known to one of skill in the art. Useful vectors may comprise constitutive or inducible promoters to direct expression of either fusion or non-fusion proteins. With fusion vectors, a number of amino acids are usually added to the expressed target gene sequence such as, but not limited to, a protein sequence for thioredoxin. A proteolytic cleavage site may further be introduced at a site between the target recombinant protein and the fusion sequence. Additionally, a region of amino acids such as a polymeric histidine region may be introduced to allow binding to the fusion protein by metallic ions such as nickel bonded to a solid support, and thereby allow purification of the fusion protein. Once the fusion protein has been purified, the cleavage site allows the target recombinant protein to be separated from the fusion sequence. Enzymes suitable for use in cleaving the proteolytic cleavage site include, but are not limited to, Factor Xa and thrombin. Fusion expression vectors that may be useful in the present invention include pGex (Amrad Corp., Melbourne, Australia), pRIT5 (Pharmacia, Piscataway, N.J.) and pMAL (New England Biolabs, Beverly, Mass.), which fuse glutathione S-transferase, protein A, or maltose E binding protein, respectively, to the target recombinant protein.

Expression of unfused foreign genes in E. coli may be accomplished with recombinant vectors including, but not limited to, the E. coli expression vector pUR278 as described in Ruther et al. (1983) E.M.B.O.J. 2: 1791, incorporated herein by reference in its entirety. Using the pUR278 vector, the nucleotide sequence coding for the Mago nashi gene product may be ligated in frame with the lacV coding region to produce a fusion protein.

Expression of a foreign gene can also be obtained using eukaryotic vectors such as mammalian, yeast or insect cells. The use of eukaryotic vectors permits partial or complete post-translational modification such as, but not only, glycosylation and/or the formation of the relevant inter- or intra-chain disulfide bonds. Examples of vectors useful for expression in the yeast Saccharomyces cerevisiae include pYepSecl as in Baldari et al., (1987), E.M.B.O.J, 6: 229–234 and pYES2 (Invitrogen Corp., San Diego, Calif.), incorporated herein by reference in their entirety.

Baculovirus vectors are also available for the expression of proteins in cultured insect cells (F9 cells). The use of recombinant Baculovirus vectors can be, or is, analogous to the methods disclosed in Richardson C. D. ed., (1995), "Baculovirus Expression Protocol" Humana Press Inc.; Smith et al. (1983) Mol. Cell. Biol. 3: 2156–2165; Pennock et al. (1984) Mol. Cell. Biol. 4: 399–406 and incorporated herein by reference in their entirety.

Mago Nashi Nucleic Acid Sequence Specific Probes

Another aspect of the present invention pertains to the use of an isolated nucleic acid molecule the sequence of which is derived from the nucleic acid sequence SEQ ID NO: 1, or degenerate variant thereof for constructing nucleotide probes and primers useful for a variety of functions. For example, synthetic oligonucleotide probes are useful for detecting complementary nucleotide sequences in biological materials such as cells, cell extracts or tissues (as well as in an in situ hybridization technique). For example, isolated nucleic acids synthesized according to the present invention can determine whether a cell expresses an mRNA transcript encoding the *Mago* protein. The present invention also contemplates the use of antisense nucleic acid molecules, which are designed to be complementary to a coding strand of a nucleic acid (i.e., complementary to an mRNA sequence) or, alternatively, complimentary to a 5' or 3' untranslated region of the mRNA. Another use of synthetic nucleotides is as primers (DNA or RNA) for a polymerase chain reaction (PCR), ligase chain reaction (LCR), or the like.

Synthesized nucleotides can be produced in variable lengths—the number of bases synthesized will depend upon a variety of factors, including the desired use for the probes or primers. Additionally, sense or anti-sense nucleic acids or oligonucleotides can be chemically synthesized using modified nucleotides to increase the biological stability of the molecule or of the binding complex formed between the anti-sense and sense nucleic acids. For example, acridine-substituted nucleotides can be synthesized. Protocols for designing isolated nucleotides, nucleotide probes, and/or nucleotide primers are well known to those of ordinary skill, and can be purchased commercially from a variety of sources (e.g., Sigma Genosys, The Woodlands, Tex. or The Great American Gene Co., Ramona, Calif.).

Nucleotides constructed in accordance with the present invention can be labeled to provide a signal as a means of detection. For example, radioactive elements such as $^{32}P$, $^{3}H$, and $^{35}S$ or the like provide sufficient half-life to be useful as radioactive labels. Other materials useful for labeling synthetic nucleotides include fluorescent compounds, enzymes and chemiluminescent moieties. Methods useful in selecting appropriate labels and binding protocols for binding the labels to the synthetic nucleotides are well known to those of skill in the art. Standard immunology manuals such as Promega: Protocol and Applications Guide, 2nd Edition, 1991 (Promega Corp., Madison, Wis.; the content of which is incorporated herein in its entirety) may be consulted to select an appropriate labeling protocol without undue experimentation.

Mago Protein-Specific Antibodies

It is further contemplated to be within the scope of the present invention to produce and use antibodies specifically reactive with a *Mago* protein or a region thereof. The antibody may be monoclonal or polyclonal and may be produced by conventional methodology using the *Mago* protein, or an immunologic fragment thereof, as an immunogen. For example, a mouse, rabbit, horse, sheep, or goat may be immunized with a *Mago* protein of the present invention, an immunogenic fragment thereof, or a *Mago* fusion protein or fragment thereof, using an immunization protocol conducive to producing antibodies reactive with the *Mago* protein or a fragment thereof. Following completion of the immunization steps, antiserum reactive with the jointed protein may be collected and, if desired, polyclonal anti-*Mago* antibodies isolated.

Antibodies that specifically bind, for example, *Mago* epitopes can also be used in immunohistochemical staining of tissue samples in order to evaluate the abundance and pattern of expression of *Mago_1*. Anti-*Mago* antibodies can be used diagnostically, for example, in immuno-precipitation and immuno-blotting to detect and evaluate *Mago* levels in tissue, bodily fluids or avian eggs. The level of *Mago* can be measured in cells isolated from bodily fluid, such as in samples of cerebral spinal fluid or blood, or can be measured in tissue, such as produced by biopsy. Diagnostic assays using anti-*Mago* antibodies can include, for example, immunoassays designed to aid in the expression of a *Mago nashi*-specific nucleic acid in a chicken or other bird.

Another application of anti-*Mago* antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of *Mago* can then be detected with antibodies, as, for example, reacting nitrocellulose filters lifted from infected plates with anti-*Mago* antibodies. Phage, scored by this assay, can then be isolated from the infected plate. Thus, the presence of *Mago* homologs can be detected and cloned from other avian sources.

Viral Vector Cell Transformation

A preferred approach for in vivo introduction of nucleic acid encoding one of the subject proteins into a cell is by use of a viral vector containing nucleic acid, e.g., a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo. These vectors provide efficient delivery of genes into cells, and the transferred nucleic acids are stably integrated into the chromosomal DNA of the host. Recombinant retrovirus can be constructed in which part of the retroviral coding sequence (gag, pol, env) has been replaced by nucleic acid encoding a *Mago* protein, thereby rendering the retrovirus replication defective. Protocols for producing recombinant retroviruses and for infecting cells in vitro or in vivo with such viruses can be found in Current Protocols in Molecular Biology, Ausubel et al. (1989) (eds.) Greene Publishing Associates, Sections 9.10–9.14, and other standard laboratory manuals. Examples of suitable retroviruses include pLJ, pZIP, pWE and pEM, all well known to those skilled in the art. Examples of suitable packaging virus lines for preparing both ecotropic and amphotropic retroviral systems include psiCrip, psiCre, psi2 and psiAm.

Furthermore, it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) Proc. Natl. Acad. Sci. 86: 9079–9083; Julan et al. (1992) J. Gen. Virol. 73: 3251–3255; and Goud et al. (1983) Virology 163: 251–254); or coupling cell surface ligands to the viral env proteins (Neda et al. (1991) J. Biol. Chem. 266: 14143–14146), and which are incorporated herein in their entireties. Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, and can also be used to convert an ecotropic vector into an amphotropic vector. Moreover, use of retroviral gene delivery can be further enhanced by the use of tissue- or cell-specific transcriptional regulatory sequences that control expression of the *Mago nashi* gene of the retroviral vector.

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, for example, Berkner et al. (1988) BioTechniques 6: 616; Rosenfeld et al. (1991) Science 252: 43 1434; and Rosenfeld et al. (1992) Cell 68: 143–155), and which are incorporated herein in their entirety. Suitable adenoviral vectors derived from the adenovirus strain Ad type 5 d1324 or other strains of adenovirus (e.g., Ad2, Ad3, Ad7 etc.) are well known to those skilled in the art. The virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J Murray, (1991) Ed. (Humana, Clifton, N.J.) vol. 7. pp. 109–127), and which are incorporated herein in their entirety. Expression of the inserted *Mago nashi* gene can be under control of, for example, the E1A promoter, the major late promoter (MLP) and associated leader sequences, the E3 promoter, or exogenously added promoter sequences.

Yet another viral vector system useful for delivery of, for example, the subject *Mago nashi* gene, is the adeno-associated virus (AAV). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790), and which are incorporated herein in their entirety.

Other viral vector systems that may have application in gene therapy have been derived from such as, but not limited to, herpes virus, vaccinia virus, and several RNA viruses. In particular, herpes virus vectors variants may provide a unique strategy for persistence of the recombinant *Mago nashi* gene in cells of the central nervous system.

Non-Viral Expression Vectors

Most non-viral methods of gene transfer rely on normal mechanisms used by eukanyotic cells for the uptake and intracellular transport of macromolecules. In preferred embodiments, non-viral gene delivery systems of the present invention rely on endocytic pathways for the uptake of the subject *Mago nashi* gene by the targeted cell. Exemplary gene delivery systems of this type include liposomal derived systems, poly-lysine conjugates, and artificial viral envelopes.

In a representative embodiment, a gene encoding the subject *Mago* protein can be entrapped in liposomes bearing positive charges on their surface (e.g., lipofectins) and (optionally) which are tagged with antibodies against cell surface antigens of the target tissue (Mizuno et al. (1992) NO Shinkei Geka 20:547–551; PCT publication WO91/06309; Japanese patent application 1047381; and European patent publication EP-A-43075), and which are incorporated herein in their entireties.

In similar fashion, the gene delivery system comprises an antibody or cell surface ligand that is cross-linked with a gene binding agent such as polylysine (see, for example, PCT publications WO93/04701, WO92/22635, WO92/20316, WO92/19749, and WO92/06180), and which are incorporated herein in their entireties. It will also be appreciated that effective delivery of the subject nucleic acid constructs via receptor-mediated endocytosis can be improved using agents which enhance escape of gene from the endosomal structures. For instance, whole adenovirus or fusogenic peptides of the influenza HA gene product can be used as part of the delivery system to induce efficient disruption of DNA-containing endosomes (Mulligan et al. (1993) Science 260–926; Wagner et al. (1992) Proc. Natl. Acad. Sci. 89:7934; and Christiano et al. (1993) Proc. Natl. Acad. Sci. 90:2122), and which are incorporated herein in their entirety.

*Mago Nashi*-Specific Nucleic Acid Probes

The nucleotide sequence determined from the cloning of subject *Mago* from a chicken (SEQ ID NO: 1) will allow for the generation of probes designed for use in identifying homologs of *Mago nashi* in other avian species.

In addition, the present invention contemplates nucleotide probes can be generated from a cloned nucleic acid sequence of the *Mago* protein, which allow for histological screening of intact tissue and tissue samples for the presence of *Mago nashi*-specific mRNA.

In one embodiment of the present invention, therefore the nucleotide sequence of the isolated DNA molecule of the present invention may be used as a probe in nucleic acid hybridization assays for the detection of the *Mago nashi* gene. The nucleotide sequence of the present invention may be used in any nucleic acid hybridization assay system known in the art, including, but not limited to, Southern blots (Southern, E. M. (1975) J. Mol. Biol. 98: 508; Northern blots (Thomas et al. (1980) Proc. Natl. Acad. Sci. 77: 5201–05); and Colony blots (Grunstein et al, (1975) Proc. Natl. Acad. Sci. 72: 3961–65, which are hereby incorporated by reference). Alternatively, the isolated DNA molecules of the present invention can be used in a gene amplification detection procedure such as a polymerase chain reaction (Erlich et al. (1991) "Recent Advances in the Polymerase Chain Reaction" Science 252: 1643–51, which is hereby incorporated by reference) or in restriction fragment length polymorphism (RFLP) diagnostic techniques, as described in Watson et al., (2d ed. 1992), Recombinant DNA, Scientific American Books, 519–522, 545–547, which is hereby incorporated by reference.

Regulation of *Mago Nashi* Expression

Another potentially useful application of the DNA molecule of the present invention is the possibility of increasing the amount of *Mago* protein present in a bird, (especially the chicken) by gene transfer. In most instances, *Mago*-specific nucleic acid will be transferred into the animal host along with promoters, inducers, and the like (which are well known and recognized techniques in the field of genetic engineering, as noted supra) to allow the cell to initiate and continue production of the genetic product protein. A DNA molecule of the present invention can be transferred into the extra-chromosomal or genomic DNA of the host.

Another aspect of the invention relates to the use of the isolated nucleic acid in "antisense" therapy. An antisense construct of the present invention can be delivered, for example, as an expression plasmid that when transcribed in the cell, produces RNA which is complementary to at least a unique portion of the cellular mRNA which encodes a *Mago* protein. Alternatively, the antisense construct can be an oligonucleotide probe which is generated ex vivo and which, when introduced into the cell, causes inhibition of expression by hybridizing with the mRNA and/or genomic sequences encoding one of the subject *Mago* proteins. Such oligonucleotide probes are preferably modified oligonucleotides that are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al. (1988) Biotechniques 6: 958–976; and Stein et al. (1988) Cancer Res. 48: 2659–2668 and which are incorporated herein in their entirety.

It is further contemplated to be within the scope of the present invention for *Mago*-expression vectors to be used as a part of a gene therapy protocol to increase *Mago* function in a cell, or alternatively, to provide an antagonist of the naturally-occurring *Mago nashi* gene, or an antisense construct. For instance, expression constructs of the subject *Mago* protein may be administered in any biologically effective carrier, e.g., any formulation or composition capable of effectively transfecting cells in vivo with a recombinant *Mago nashi* gene. Approaches include insertion of the subject gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g., antibody conjugate), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g., locally or systemically.

Trangenic Animals

Another aspect of the present invention concerns transgenic animals, such as chickens that contain a transgene of the present invention and which preferably (though optionally) express the subject *Mago nashi* in one or more cells in the animal. In embodiments of the present invention, therefore, the expression of the transgene is restricted to specific subsets of cells, tissues or developmental stages utilizing, for example, cis-acting sequences that control expression in the desired pattern. In the present invention, such mosaic expression of the subject *Mago* proteins can be essential for many forms of lineage analysis and can additionally provide a means to assess the effects of *Mago* mutations or overexpression that might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques that allow for the expression of transgenes can be regulated via site-specific genetic manipulation in vivo are well known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject receptor. For example, excision of a target sequence that interferes with the expression of the receptor can be designed to activate expression of that protein. This interference with expression of the subject protein can result from a variety of mechanisms, such as spatial separation of the *Mago nashi* gene from the promoter element or an internal stop codon. Moreover, the transgene can be made wherein the coding sequence of the *Mago nashi* gene is flanked by recombinase recognition sequences and is initially transfected into cells in a 3' to 5' orientation with respect to the promoter element. In such an instance, inversion of the target sequence will reorient the subject *Mago nashi* gene by placing the 5' end of the coding sequence in an orientation with respect to the promoter element that allow for promoter driven transcriptional activation.

In an illustrative embodiment, either the cre/loxP recombinase system of bacteriophage P1 (Lakso et al. (1992) Proc. Natl. Acad. Sci. 89:6232–6236; Orban et al. (1992) Proc. Natl. Acad. Sci. 89:6861–6865) or the FLP recombinase system of *Saccharomyces cerevisiae* (O'Gorman et al. (1991) Science 251:1351–1355; PCT publication WO 92/15694), and which are incorporated herein in their entireties, can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements that are subject to regulatory control, e.g., tissue-specific, developmental stage-specific, and inducible or repressible by externally added agents. This regulated control will result in genetic recombination of the target sequence only in cells where recombinase expression is mediated by the promoter element. Thus, the activation of expression of the recombinant UBC9 gene can be regulated via regulation of recombinase expression.

Use of the these recombinase systems to regulate expression of, for example, a dominant negative *Mago nashi* gene, or an antisense gene, requires the construction of a transgenic animal containing transgenes encoding both the Cre recombinase and the subject gene. Animals containing both the Cre recombinase and the *Mago nashi* genes can be provided through the construction of "double" transgenic animals. A convenient method for providing such animals is to mate two transgenic animals each containing a transgene, e.g., one harboring the *Mago nashi* gene, and the other harboring the recombinase gene.

One advantage derived from initially constructing transgenic animals containing a *Mago nashi* transgene in a recombinase-mediated expressible format derives from the likelihood that the subject *Mago nashi* protein, whether antagonistic or agonistic, will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues, or in a developmentally restricted pattern.

Similar conditional transgenes can be provided using prokaryotic promoter sequences which require prokaryotic proteins to be simultaneously expressed in order to facilitate expression of the transgene. Operators present in prokaryotic cells have been extensively characterized in vivo and in vitro and can be readily manipulated to place them in any position upstream from or within a gene by standard techniques. Such operators comprise promoter regions and regions which specifically bind proteins such as activators and repressors. One example is the operator region of the lexA gene of *E. coli* to which the LexA polypeptide binds. Other exemplary prokaryotic regulatory sequences and the corresponding trans-activating prokaryotic proteins are given in U.S. Pat. No. 4,833,080. Thus, as described above for the recombinase-mediated activation, silent transgenic animals can be created which harbor the subject transgene under transcriptional control of a prokaryotic sequence that is not appreciably activated by eukaryotic proteins. Breeding of this transgenic animal with another animal that is transgenic for the corresponding prokaryotic trans-activator, can permit activation of the *Mago nashi* transgene. Moreover, expression of the conditional transgenes can be induced by gene therapy-like methods (such as those described above) wherein a gene encoding the trans-activating protein, e.g., a recombinase or a prokaryotic protein, is delivered to the tissue and caused to be expressed, such as in a cell type-specific manner.

Additionally, inducible promoters can be employed, such as the tet operator and the metallothionein promoter which can be induced by treatment with tetracycline and zinc ions, respectively (Gossen et al. (1992) Proc. Natl. Acad. Sci. 89:5547–5551; and Walden et al. (1987) Gene 61:317–327), and which are incorporated herein in their entirety.

"Knock-Out" Animals

Methods of making knock-out or gene-disruption transgenic animals are also generally known. See, for example, Manipulating the Mouse Embryo, (Cold Spring Harbor Laboratory Press, Cold Spring Harbor, N.Y., 1986). Recombinase-dependent knockouts can also be generated, e.g., by homologous recombination to insert recombinase target sequences flanking portions of an endogenous *Mago nashi* gene, such that tissue-specific and/or temporal control of inactivation of a *Mago allele* can be controlled as above. Furthermore, the present invention, by making available purified and recombinant forms of the subject *Mago* proteins, will allow the development of assays which can be used to screen for drugs which either agonize or antagonize the function of *Mago* in vivo.

Assay for *Mago* Activity Modulators

Assays for the measurement of *Mago* can be generated in many different forms, and include assays based on cell-free systems, e.g., purified proteins or cell lysates, as well as cell-based assays which utilize intact cells. Such agents can be used, for example, in the treatment of diabetic or feeding disorders, proliferative and/or differentiative disorders, and to modulate cellular metabolism.

In many drug screening programs which test libraries of compounds and natural extracts, high throughput assays are desirable to maximize the number of compounds surveyed in a given period of time. Assays performed in cell-free systems, such as may be derived with purified or semi-purified proteins or with lysates, are often preferred as "primary" screens in that they can be generated to permit rapid development and relatively easy detection of an alteration in a molecular target that is mediated by a test compound. The effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, potential inhibitors of *Mago* function can be detected in a cell-free assay generated by constitution of a functional *Mago*/target nucleic acid sequence in a cell lysate.

The present invention is further illustrated by the following examples, which are provided by way of illustration and should not be construed as limiting. The contents of all references, published patents and patents cited throughout the present application are hereby incorporated by reference in their entirety.

EXAMPLE 1

Cloning of cDNAs Containing an IRSBP Coding Sequence

Freshly laid fertilized white Leghorn chicken (*Gallus gallus*) eggs were incubated for 7 days (E7 embryonic stage). E7 embryos were dissected from the yolk and immediately flash frozen in liquid nitrogen. Total RNA was collected by homogenizing the embryos in RNA STAT-60 (Tel-Test, Inc., Friendswood, Tex.) and extracting with chloroform, following the manufacturers recommended protocol. PolyA RNA was selected by passing total RNA through oligo-dT magnetic beads (µMACs mRNA Isolation Kit, Miltenyi Biotech Inc., Auburn, Calif.) following the manufacturers recommended protocol. cDNA was synthesized using reverse transcriptase and LD PCR and ligated into λTrip1Ex2 arms using the SMART cDNA Library Construction Kit (Clontech Laboratories, Inc., Palo Alto, Calif.) following the protocols in the user manual. The resulting lambda library was packaged using a Gigapack III Gold Packaging Extract (Stratagene, La Jolla, Calif.), following the protocols in the instruction manual, and the library was amplified and titered using *E. coli* XL-1 Blues.

EXAMPLE 2

Sequencing Isolated Clones

Individual plaques were isolated and phage were eluted in 0.5 ml lambda dilution buffer (100 mM NaCl, 10 mM $MgSO_4$, 35 mM Tris, pH 7.5). cDNA inserts were amplified in a 50 μl reaction using 5 μl elution, 0.1 μM 5' primer having the sequence 5'-TCCGAGATCTGGACGAGC-3' (SEQ ID NO: 3), 0.1 mM 3' primer having the sequence 5'-TAATACGACTCACTATAGGG-3' (SEQ ID NO: 4), and 25 μl Taq PCR Master Mix (Qiagen Inc., Valencia, Calif.) (1.25 units Taq DNA polymerase, 200 μM each dNTP, and Tris buffer (pH 8.7) with KCl, $(NH4)_2SO_4$, and 1.5 mM $MgCl_2$) using the GeneAmp PCR System 9700 (Applied Biosystems, Foster City, Calif.) (30 cycles: 94° C./1 min, 50° C./1 min, 72° C./2 min). Unincorporated primers and nucleotides were removed using a QIAquick 96 PCR Purification Kit (Qiagen Inc.).

The sequencing reactions were performed from the 5' end in a half reaction (10 μl) using 1–2.5 μl purified product, 3.5–4 pmol primer having the sequence 5'-CTCGGGAAGCGCGCCATTGTGTTGGT-3' (SEQ ID NO: 5), and 4 μl BigDye Terminator Ready Reaction Mix (Applied Biosystems) following the cycle sequencing protocol for PCR products using the GeneAmp PCR System 9700. A high throughput method for sequencing 96 samples simultaneously using the ABI 3700 Genetic Analyzer (Applied Biosystems) was employed. Ease and efficiency were improved by using a 96-well format for all procedures.

For lambda libraries, plaques were eluted overnight in Qiagen 96-well round well blocks. For other libraries, DNA was extracted in 96-well flat bottom plates. The insert was then amplified from the plaque elution or DNA by PCR using a GeneAmp PCR System 9700 (Applied Biosystems). After amplification, unincorporated primers and nucleotides are removed using a Qiagen QIAquick 96 PCR purification kit. The purified PCR product was then quantified using a UV transparent plate in a plate reader that can measure absorbance in the UV range. The cycle sequencing reaction was completed using the Big Dye Terminator Kit (Applied Biosystems) and 10–100 ng of PCR product in the Gene-Amp PCR System 9700 (Applied Biosystems). Finally, unincorporated primers and nucleotides were removed with a Qiagen 96 DyeEx Dye-Terminator Removal Kit.

The clone sequences of one sequencing run from a lambda E7 library are summarized in Table 1, as follows:

TABLE 1

Sequences of One Sequencing Run From a Lambda E7 Library

| | Number of clones | Insert (bp) |
|---|---|---|
| Genes with known identity and function | | |
| 40S ribosomal genes (S6, S13, S15A, S25) | 6 | 800–1100 |
| 60S ribosomal genes (L6, 8, 9, 11, 14, 19, 21, 30, 32, 44, P1, 2) | 17 | 450–1100 |
| Hemoglobin genes (alpha A, alpha D, pi, beta, epsilon) | 14 | 750–950 |
| Metabolic genes (no duplicate clones) | 17 | |
| Nuclear genes (histone, nucleosome assembly, hnRNP) | 3 | 1050, 1100, 1500 |
| Cytoskeletal genes (f-actin capping alpha-1 subunit) | 1 | 1000 |
| Translation genes (translation initiation factor) | 1 | 750 |
| Intracellular signaling genes (MAPKK-protein kinase) | 1 | 1700 |
| Plasma membrane genes (loocyte) | 1 | 1750 |
| Germline genes (mago-nashi) | 1 | 900 |
| Lens specific genes (alpha B crystalline) | 1 | 1900 |
| Neuronal genes (3.1) | 1 | 2200 |
| Genes with known identity but little known function | | |
| Chromosome 21 orf 59 | 1 | 1500 |
| KIAA0101 | 1 | 800 |
| KIAA1424 | 1 | 2200 |
| CG14037 | 1 | 900 |
| FLJ10618 | 1 | 2000 |
| Genes with no known identity or function | 10 | 400, 500, 550, 600, 600, 1000, 1100, 1250, 1250, 1250 |

Data were converted to text files, formatted to FASTA, and each nucleotide sequence translated in all reading frames was compared to the protein sequence database using BLAST 2.05 (NCBI).

EXAMPLE 3

SEQUENCE COMPARISONS

The protein sequence SEQ ID NO: 2 derived from the nucleic acid sequence SEQ ID NO: 1 was aligned with the equivalent *Mago homologs* from *X. laevis* (SEQ ID NO 6; GenBank Accession No. AF007860), *H. sapiens* (SEQ ID NO: 7; GenBank Accession No. AF067173), *M. musculus* (SEQ ID NO 8; GenBank Accession No. AF007862), and *D. melangogaster* (SEQ ID NO: 9; GenBank Accession No. U03559). The sequences were aligned, with gaps introduced where necessary, to maximize the similarities. The results are illustrated in FIG. 3.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. An isolated nucleic acid comprising a sequence, that encodes a polypeptide with the amino acid sequence of SEQ ID NO: 2.

2. The isolated nucleic acid of claim 1 comprising the nucleotide sequence SEQ ID NO: 1.

3. The isolated nucleic acid of claim 1 comprising a sequence having at least 75% identity to SEQ ID NO: 1.

4. The isolated nucleic acid of claim 1 comprising a sequence having at least 95% identity to SEQ ID NO: 1.

5. The isolated nucleic acid of claim 1 comprising a sequence having at least 99% identity to SEQ ID NO: 1.

6. The isolated nucleic acid of claim 1, wherein the nucleic acid is isolated from a bird.

7. The isolated nucleic acid of claim 6, wherein the bird is a chicken.

8. The isolated nucleic acid of claim 1 operably linked to a heterologous nucleic acid.

9. The isolated nucleic acid of claim 8, wherein the heterologous nucleic acid is selected from the group consisting of a promoter, an enhancer, and a transcription activator.

10. A vector comprising the isolated nucleic acid of claim 1.

11. The vector of claim 10, wherein the vector is an expression vector.

12. The vector of claim 10, wherein the nucleic acid is operably linked to an expression control sequence, wherein the expression control sequence directs production of a transcript from said nucleic acid.

13. A cultured cell comprising the vector of claim 10, or a progeny of said cell, wherein the cell or the progeny of the cell expresses the polypeptide encoded by the vector.

14. The cultured cell or progeny of said cell of claim 13, wherein the cultured cell is selected from a mammalian vertebrate cell, a non-mammalian vertebrate cell, a yeast cell and an insect cell.

15. The cultured cell or a progeny of said cell of claim 13, wherein the cultured cell is an avian embryonic cell.

16. A method of producing a protein, comprising culturing the cell or progeny of said cell of claim 13 under conditions permitting expression of the protein, and purifying the polypeptide from the cell or progeny of said cell or the medium of the cell.

17. A method for identifying a nucleic acid homolog comprising the steps of:
   a. obtaining a nucleic acid sequence probe molecule having a nucleotide sequence, said nucleotide sequence comprising the sequence selected from SEQ ID NO: 1, the complement sequence thereof, or a degenerate variant thereof;
   b. accessing a sequence database comprising a target nucleotide sequence;
   c. aligning said nucleic acid sequence probe molecule with said target nucleotide sequence;
   d. determining a percent identity between a nucleotide sequence of said nucleic acid sequence probe molecule and said target nucleotide sequence; and
   e. identifying said target nucleotide sequence in said sequence database wherein the percent similarity between the nucleotide sequence of said nucleic acid sequence probe molecule and said target nucleotide sequence has at least 80% identity to SEQ ID NO: 1.

18. The method as in claim 17, wherein the percent identity between the nucleotide sequence of said nucleic acid sequence probe molecule and said target nucleotide sequence has at least 90% identity to SEQ ID NO: 1.

19. The method as in claim 17, wherein the percent identity between the nucleotide sequence of said nucleic acid sequence probe molecule and said target nucleotide sequence has at least 95% identity to SEQ ID NO: 1.

20. The method as in claim 17, wherein the percent identity between the nucleotide sequence of said nucleic acid sequence probe molecule and said target nucleotide sequence has at least 99% identity to SEQ ID NO: 1.

* * * * *